United States Patent [19]

Meilland

[11] Patent Number: Plant 6,814

[45] Date of Patent: May 23, 1989

[54] ROSE PLANT—MEIZALEO VARIETY

[75] Inventor: Alain A. Meilland, Antibes, France

[73] Assignee: The Conard-Pyle Company, West Grove, Pa.

[21] Appl. No.: 144,029

[22] Filed: Jan. 14, 1988

[51] Int. Cl.[4] ..... A01H 5/00

[52] U.S. Cl. ..... Plt./22

[58] Field of Search ..... Plt./22

*Primary Examiner*—James R. Feyrer

*Attorney, Agent, or Firm*—Burns, Doane, Swecker & Mathis

[57] ABSTRACT

A new and distinct variety of Floribunda rose plant is provided which abundantly forms attractive long lasting semi-double blossoms. The blossoms are light chrome yellow in coloration and bear a margin which is more or less suffused with light vermilion red. The plant grows rapidly and exhibits vigorous vegetation. The new variety is particularly well suited for cut flower production and forces well during the winter.

1 Drawing Sheet

SUMMARY OF THE INVENTION

The new variety of Floribunda rose plant was created by artificial pollination wherein two parents were crossed which previously had been studied in the hope that they would contribute the desired characteristics. The female parent (i.e., the seed parent) of the new variety was the Sweet Promise variety (U.S. Plant Pat. No. 3,095). The male parent (i.e., the pollen parent) of the new variety was formed by pollinating the Sweet Promise variety with pollen from the Golden Garnette variety (U.S. Plant Pat. No. 1,898). The parentage of the new variety can be summarized as follows:

Sweet Promise × [Sweet Promise × Golden Garnette].

In the United States the Sweet Promise variety commonly is known as the Sonia variety.

The seeds resulting from the above pollination were sown and 343 plantlets were obtained which were physically and biologically different from each other. Selective study resulted in the identification of a single plant of the new variety.

The new variety meets well the needs of the horticultural industry for all uses, and is particularly well suited for cut flower production.

It was found that the new variety of Floribunda rose plant of the present invention possesses the following combination of characteristics:

(a) forms attractive long lasting blossoms which are chrome yellow in coloration and bear a petal margin which is more or less suffused with light vermilion red,
(b) forces well and is particularly well suited for cut flower production, and
(c) exhibits a vigorous growth habit.

The new variety has been found to undergo asexual propagation by a number of routes, including budding, grafting, cuttage, etc. The characteristics of the new variety have been found to be strictly transmissible by such asexual propagation from one generation to another.

The new variety has been named the Meizaleo variety.

BRIEF DESCRIPTION OF PHOTOGRAPH

The accompanying photograph shows as nearly true as it is reasonably possible to make the same, in a color illustration of this character, typical specimens of the plant parts of the new variety. The rose plants of the new variety were two years of age and observed during June while grafted on Rose indica understock and growing in a greenhouse at Cap d'Antibes, France.

DETAILED DESCRIPTION

Figures 1, 2, 3, 4, 5, 6, 7, 8, 9, 10, 11, 12, 13, 14, 15, 16:
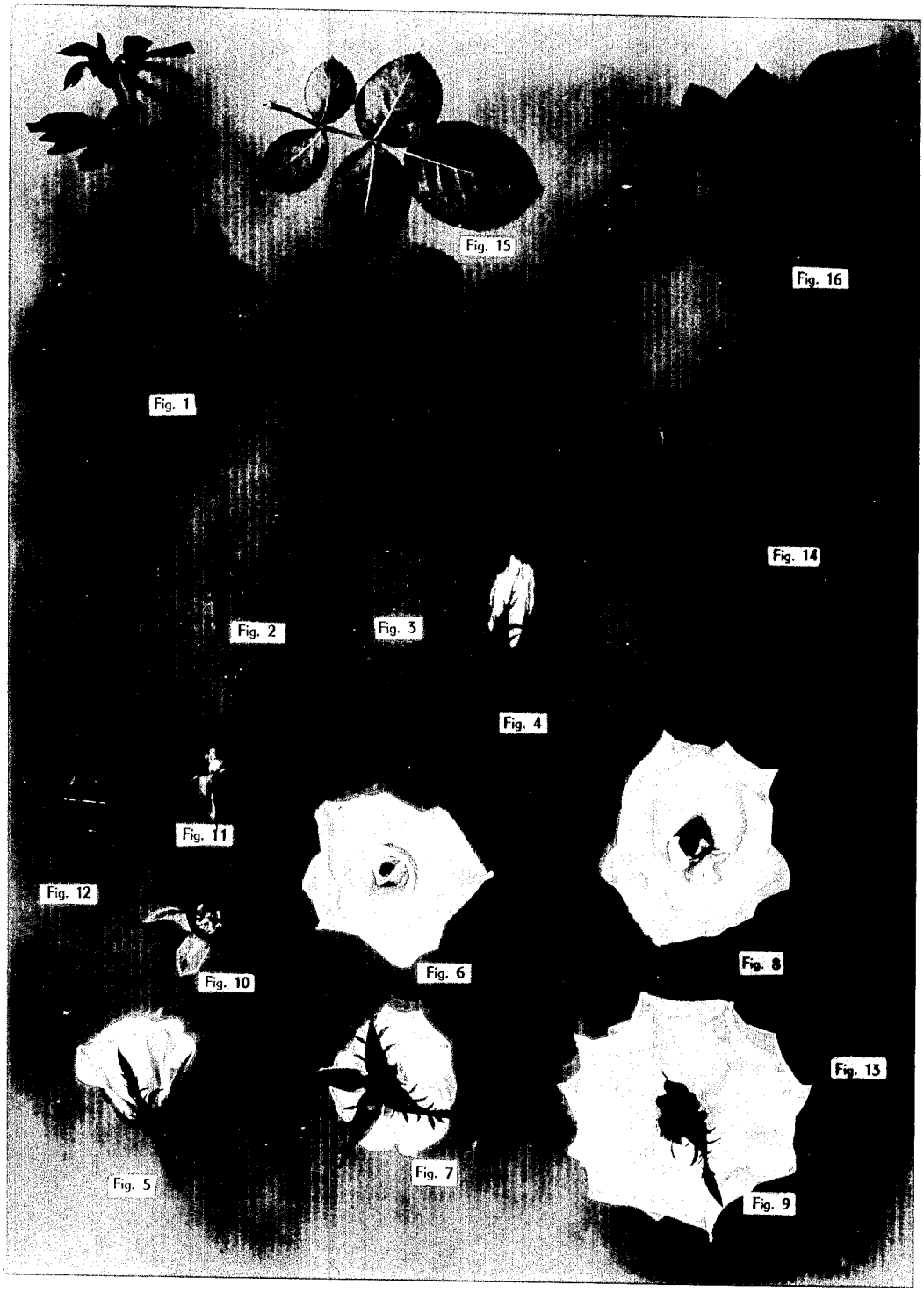
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of a fully open flower — plan view — obverse.
FIG. 7 illustrates a specimen of a fully open flower — plan view — reverse.
FIG. 8 illustrates a specimen of a fully open flower immediately prior to petal drop-plan view — obverse; verse.
FIG. 9 illustrates a specimen of a fully open flower immediately prior to petal drop — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates specimens of leaves with three leaflets — upper and under surfaces.
FIG. 15 illustrates specimens of leaves with five leaflets — upper and under surfaces.
FIG. 16 illustrates a specimen of a leaf with seven leaflets — plan view — upper surface.

The chart used in the identification of the colors is that of The Royal Horticultural Society (R.H.S. Colour Chart). The terminology which precedes reference to the chart has been added to indicate the corresponding color in more common terms. The description is based on two year old specimens of the new variety during June while grafted on *Rosa indica* understock and growing in a greenhouse at Cap d'Antibes, France.

Class: Floribunda.

Plant:

*Height.*—Plants which were pruned to a height of 85 cm. produce floral stems having a length of approximately 20 to 40 cm.

*Habit.*—Semi-erect.

Branches:

*Color.*—Young stems: light green, Green Group 143C. Adult wood; bronzed green, Yellow-Green Group 146A.

Leaves:

*Stipules.*—Adnate, pectinate, narrow and linear.

*Petioles.*—Upper surface: grooved, reddish brown on young foliage and medium green on adult foliage with more or less glandular edges. Under surface: light green, with some thorns.

*Leaflets.*—Number: 3 and 5 (most often). Shape: oval. Serration: simple and regular. Texture: firm. General appearance: dense foliage which is semi-glossy. Color (young foliage): Upper surface: reddish brown. Under surface: reddish brown. Color (adult foliage): Upper surface: dark green, Green Group 137A. Under surface: light green, Green group 137C.

Inflorescence:

*Number of flowers.*—Commonly 1 to 5 per stem.

*Peduncle.*—Straight, rigid, medium green, more less tinted with red, bears thorns intermingled with glandular ariculas, approximately 10 to 11 cm. in length on average.

*Sepals.*—Upper surface: tomentose and greenish in coloration. Under surface: light green in coloration and the outside sepals have appendiculated edges.

*Buds.*—Shape: conical, lengthened. Length: approximately 2 cm. on average. Size: small. Color upon opening: Upper surface: light lemon yellow, Yellow-Orange Group 14C, suffused with light vermilion red, Red Group 44D. Under surface: light golden yellow, Yellow Group 12C, more or less suffused with vermilion red, Red Group 44D.

*Flower.*—Shape: opens initially as a hollow cup and subsequently assumes the configuration of a flattened cup. Diameter: approximately 8 to 9 cm.

on average. Color (when opening begins): Upper surface: light chrome yellow, Yellow-Orange Group 14D, slightly suffused with light vermilion, Red Group 44D, clearing to white on the external petals. Under surface: mimosa yellow, Yellow Group 8C. Color (when partially open): Upper surface: light chrome yellow, Yellow-Orange Group 14D, slightly suffused with light vermilion, Red Group 44D, clearing to white on the external petals. Under surface: mimosa yellow, Yellow Group 8C. Color (at end of opening): Upper surface: light chrome yellow, Yellow-Orange Group 14D, slightly suffused with light vermilion, Red Group 44D, clearing to white on the external petals. Under surface: mimosa yellow, Yellow Group 8C. Fragrance: none. Lasting quality: long. Petal drop: adequate. Petal number: approximately 12 to 15 on average. Petal texture: firm. Petal form: generally rounded with reflected tips. Stamen number: approximately 120 to 123 on average. Anthers: normal, ochre, and edged with orange-red coloration. Pistils: approximately 80 to 84 on average. Stigmas: normal, straw colored, commonly located beyond the stamens. Styles: straw colored with fuchsine tips, and of irregular heights. Receptacle: medium green in coloration, smooth at the dehiscence of the anthers, and in a longitudinal section it is funnel shaped.

Development:

*Vegetation.*—Vigorous.

*Blooming.*—Abundant especially in the winter.

*Resistance to diseases.*—Good.

*Aptitude to forcing.*—Excellent.

I claim:

1. A new and distinct variety of Floribunda rose plant characterized by the following combination of characteristics:

(a) forms attractive long lasting blossoms which are chrome yellow in coloration and bear a petal margin which is more or less suffused with light vermilion red, (b) forces well and is particularly well suited for cut flower production, and (c) exhibits a vigorous growth habit;

substantially as herein shown and described together with the parts thereof.

* * * * *